(12) United States Patent
Kuraya et al.

(10) Patent No.: US 7,087,812 B1
(45) Date of Patent: Aug. 8, 2006

(54) VECTORS FOR TRANSFORMING PLANTS

(75) Inventors: Yoshiki Kuraya, Sizuoka (JP); Toshihiko Komari, Sizuoka (JP); Yukoh Hiei, Sizuoka (JP)

(73) Assignee: Japan Tobacco Inc., Tokyo (JP)

(*) Notice: Subject to any disclaimer, the term of this patent is extended or adjusted under 35 U.S.C. 154(b) by 0 days.

(21) Appl. No.: 09/856,976

(22) PCT Filed: Sep. 30, 1999

(86) PCT No.: PCT/JP99/05386

§ 371 (c)(1),
(2), (4) Date: May 30, 2001

(87) PCT Pub. No.: WO01/25459

PCT Pub. Date: Apr. 12, 2001

(51) Int. Cl.
*A01H 1/00* (2006.01)
*C12N 15/82* (2006.01)
*C12N 1/20* (2006.01)
*C07H 2/04* (2006.01)

(52) U.S. Cl. .............. 800/294; 800/295; 800/278; 435/252.3; 435/320.1; 536/23.1

(58) Field of Classification Search .............. 536/23.1; 800/294, 298; 435/252.3, 320.1
See application file for complete search history.

(56) References Cited

FOREIGN PATENT DOCUMENTS

WO WO 99/25855 5/1999

OTHER PUBLICATIONS

Becker, D. New palnt binary vectors with selectable markers located proximal to the left T-DNA border. P. Molecular Biology 20:1195-1197 (1992).*
Gartland in Methods in Molecular Biology vol. 44, pp. 15-28, 1995, Humana Press, Totowa NJ.*
Plant Cell, 6, 1994. Martineau B. et al., pp. 1032-1033.
Plant Molecular Biology, 34, 1997, Wenck Allan et al., pp. 913-922.
Proc. Natl. Acad. Sci. USA, 83, 1986, Horsch RB et al., pp. 4428-4432.
Proc. Natl. Acad, Sci, USA, 83, Jun. 1986, George C. Jen et al., pp. 3895-3899.
Cell, 57, Jun. 2, 1989, Gees Bakkeren et al., pp. 847-857.
The Plant Journal, Maria E. Konov et al., (1997), pp 945-957.
Database BIOSIS on DIALOG, No. 19990483906 Hanson Bill et al., 19 (6) Sep., 1999 pp. 727-734.
Database BIOSIS on DIALOG, No. 199598547959 Ramanathan V. et al., 28 (6) 19995, pp. 1149-1154.

* cited by examiner

*Primary Examiner*—Phuong T. Bui
*Assistant Examiner*—Georgia L. Helmer
(74) *Attorney, Agent, or Firm*—Birch, Stewart, Kolasch & Birch, LLP

(57) ABSTRACT

Vectors for transforming plants with the use of *agrobacteria* which have been modified so as to elevate the possibility of the recognition of the border sequences of the vectors by vir proteins of the *agrobacteria*, thereby lowering the possibility of the transfer of DNAs other than T-DNA into plant chromosomes. More particularly, the above-vectors are those to be used in transforming plants which have right and left border sequences which can be recognized by the vir proteins of the *agrobacteria*, a T-DNA sequence which is located between these border sequences and into which a gene to be transferred into plants can be inserted, and a replication origin enabling the replication of the vectors in bacteria, characterized by having a plural number of left border sequences.

8 Claims, 2 Drawing Sheets pSLB0 pSLB2 pSLB3

VECTORS FOR TRANSFORMING PLANTS

This application is the national phase under 35 U.S.C. § 371 of PCT International Application No. PCT/JP00/05386 which has an International filing date of Sep. 30, 1999, which designated the United States of America and was not published in English.

TECHNICAL FIELD

The present invention relates to plant transformation vectors, more particularly, vectors useful in *Agrobacterium*-mediated plant transformation. The invention further relates to a method of transforming plants using the vectors. The invention is particularly useful for generating transgenic plants that may be taken as food.

BACKGROUND ART

It has long been known that *Agrobacterium* (*Agrobacterium tumefaciens*), is a soil bacterium which causes Crown gall disease in many dicotyledonous plants. In the ninety-seventies, it was found that the Ti plasmid of *Agrobacterium* is involved in pathogenicity and that T-DNA which is part of the Ti plasmid is integrated into the plant genome. It was later revealed that the T-DNA contained the hormone synthesis genes (cytokinins and auxins) necessary for crown gall tumorigenesis and that those genes, although derived from bacteria, are expressed in plants. A group of genes that are located in the virulence region (Vir region) of the Ti plasmid are necessary to the excision of T-DNA and its transfer to plants, and furthermore, the border sequences that are located on opposite ends of T-DNA are required for the excision, which are called the right border sequence and the left border sequence. *Agrobacterium rhizogenes*, another *Agrobacterium* species has a similar system involving the Ri plasmid.

Stated more specifically, the proteins produced on the basis of the genes located in the vir region (vir proteins) recognize the right and left border sequences to integrate the T-DNA located between the border sequences into plant genome. This function provided the basis for the transformation of plants with a foreign gene pre-inserted into T-DNA, thereby giving rise to the development of *Agrobacterium*-mediated plant transformation technology.

Most recently, however, several reports have appeared describing that, in certain kinds of plants, it is sometimes observed that T-DNA is not excised at the border sequences, and hence, T-DNA can be transferred into the plant chromosome together with a region adjacent to T-DNA (Ramanathan et al., Plant Molecular Biology 28, 1149–1154 (1995), and Kononov et al., Plant Journal 11, 945–957 (1997)). If a DNA element other than T-DNA is co-transferred, the resulting transgenic plants will be suspected of having unexpected characteristics, which could have a negative impact on public acceptance of food products made of transgenic plants. It is therefore desired to develop a method whereby it can be ensured that unnecessary non-T-DNA sequences of *Agrobacterium* will not transfer to plant chromosomes.

The inventors supposed that the vir proteins of *Agrobacterium* sometimes fail to recognize the border sequences and this may explain the reason why non-T-DNA is transferred into plant chromosome together with T-DNA. No vectors have yet been developed that can suppress or reduce the transfer of non-T-DNA segment with a view to solving said problem.

Based on the above supposition, the inventors have conducted intensive studies for creating vectors for use in *Agrobacterium*-mediated transformation. In order to reduce the probability that non-T-DNA element is transferred to plant chromosome the inventors modified the vector with a view to increasing the efficiency of the vir proteins of *Agrobacterium* to recognize the border sequence/s. As a result, it has been found that while two border sequences exist in the transformation vector, the probability of the integration of non-T-DNAs can be reduced by providing a plurality of left border sequences. The present invention has been accomplished on the basis of this finding.

SUMMARY OF THE INVENTION

The present invention provides a plant transformation vector based on the function of *Agrobacterium*, wherein the left border sequence has been modified such as to reduce the possibility of the integration of any non-T-DNA segment into plant chromosomes. More particularly, the invention provides a plant transformation vector comprising a right border sequence and a left border sequence that can be recognized by the vir proteins of *Agrobacterium*, a T-DNA region located between these border sequences and into which a gene to be introduced into the plant can be inserted, and a replication origin (ori) that enables replication of said vector in bacteria (e.g. *Agrobacterium* and bacteria for vector amplification), wherein said left border sequence has been modified such as to reduce the possibility of integration of any non-T-DNA sequence into plant chromosomes.

Figure 1:
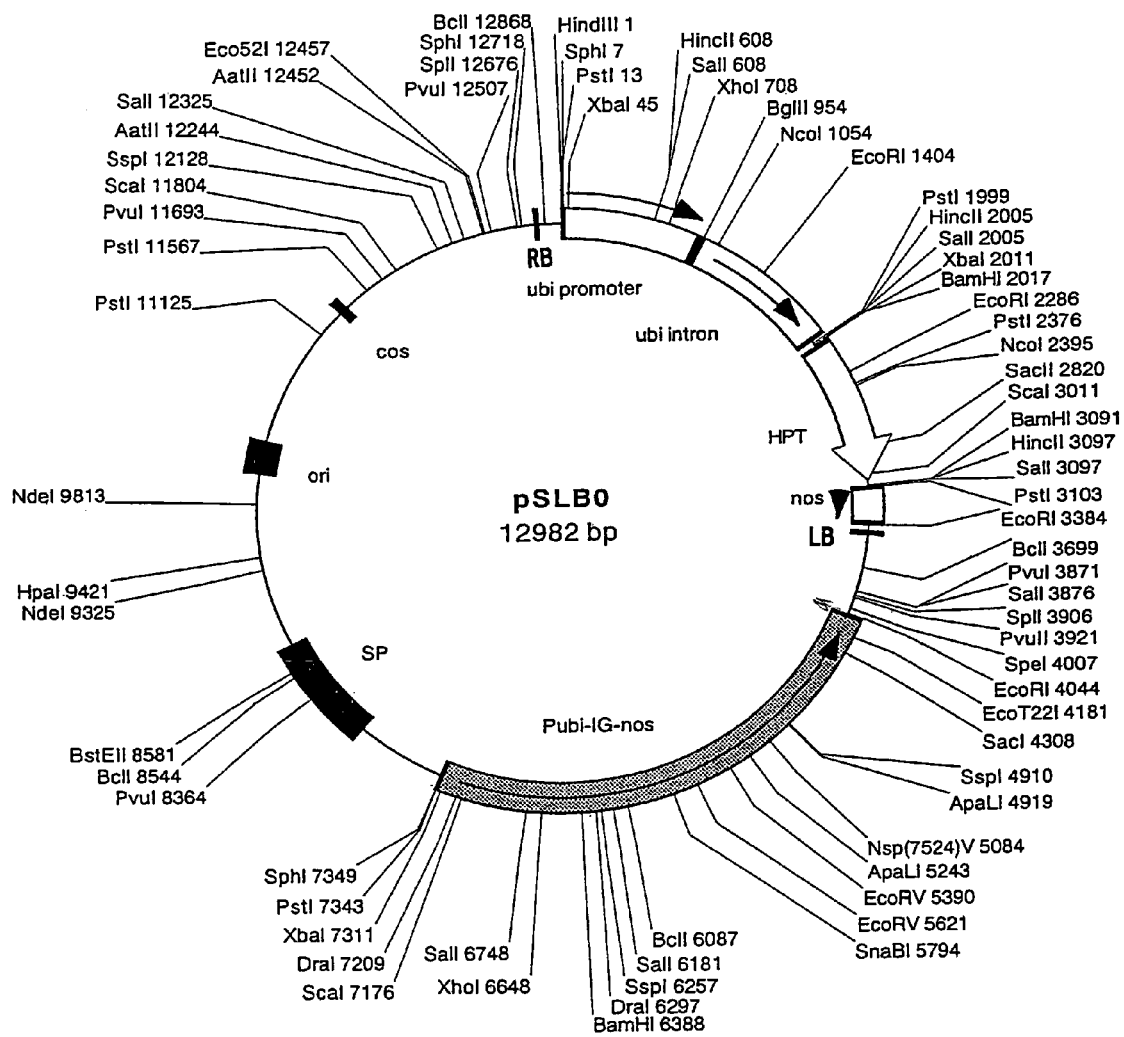
FIG. 1 shows vector pSLB0 used in the Example; this vector was prepared from pSB11 by modifying it to have within the T-DNA region a cassette, for expressing the hygromycin resistance gene under control of a ubiquitin promoter and a ubiquitin intron, then inserting a cassette for expressing the GUS gene containing a catalase intron under control of a ubiquitin promoter, at the site recognizable by restriction enzyme StuI.

DETAILED DESCRIPTION OF THE INVENTION (1) Vector Preparation

The vector of the invention has the left border sequence modified to operate such as to reduce the possibility of the integration of an unnecessary DNA sequence/s, i.e. a non-T-DNA sequence/s into plant chromosomes. In a preferred embodiment, the invention provides the vectors having the left border sequence modified such as to comprise the placement of more than one DNA sequence that can be recognized by vir proteins (e.g. a known left border sequence).

DNA fragments comprising more than one left border sequence can be prepared by various known methods on the basis of known border sequences. For example, one can synthesize a single-stranded DNA molecule having the same sequence as a left border sequence which is contained in an available Ti plasmid, prepare the double-stranded DNA molecule from the single strand, and if necessary, link two or more of such double-stranded DNAs together. The obtained DNA fragment can be then inserted into a plant transformation vector at a suitable restriction site nearby up/downstream of the existing left border sequence located downstream of the T-DNA region. In this way, the vector of the invention can be easily constructed.

The plant transformation vector from which the vector of the invention can be prepared by modifying its left border sequence should at least have a right and a left border sequences that can be recognized by vir proteins, a T-DNA sequence located between the right and left border sequences and into which can be inserted a gene to be introduced into the plant, and a replication origin that can operate in bacteria for replication of the vector (e.g. *Escherichia coli*). The preferred plant transformation vector has a replication origin that can operate in *Agrobacterium*.

As long as these requirements are satisfied, various vectors can be modified on the left border sequence. For example, the various vectors used in the following plant transformation methods based on *Agrobacterium* can be modified:

(i) a small intermediate cloning vector having right and left border sequences and which has a foreign gene inserted into T-DNA, and an acceptor Ti plasmid having the vir region are subjected to homologous recombination to prepare a hybrid Ti plasmid vector, and the plant is infected with *Agrobacterium* containing the hybrid Ti plasmid vector;

(ii) a foreign gene is inserted into the T-DNA region of a small Ti plasmid having no vir region (the plasmid is commonly called a mini plasmid or a micro Ti plasmid and is capable of replication in many bacteria) and the plasmid is introduced into *Agrobacterium* which harbors a plasmid having the vir region but no T-DNA, and the plant is infected with the *Agrobacterium* containing the two plasmids;

(iii) a small intermediate cloning vector having a right and a left border sequences and which has an foreign gene inserted into T-DNA, and an acceptor Ti plasmid having a portion of the vir region (i.e., vir gene lacking a portion of the full length of the vir region) are subjected to homologous recombination to prepare a hybrid Ti plasmid vector, the hybrid Ti plasmid vector is introduced into *Agrobacterium* which has the vir region (full length) harboring but T-DNA deficient plasmid introduced in it, and the plant is infected with the *Agrobacterium* containing the two plasmids. The various vectors used in these methods can be modified on the left border sequence. Small Ti plasmids with a modification on the left border sequence are easy to handle in operations such as for modifying the foreign gene in T-DNA and hence are a preferred embodiment of the vector of the invention. Examples of such small Ti plasmids include pBI101 and pBI121 (both being available from CLONTECH), as well as pSB11 which was used in the Example to be described later.

The concept of the invention is applicable not only to the Ti plasmid but also to the Ri plasmid.

The vector of the invention may contain a marker gene in the T-DNA sequence that permits selection of the transformant, such as an antibiotic resistance gene or a luminescence gene. To be specific, commonly used marker genes may be employed in the usual manner and they include antibiotic resistance genes such as those conferring resistance to tetracycline, ampicillin, kanamycin, neomycin, hygromycin and spectinomycin, and luminescence genes such as the luciferase gene, β-galactosidase, green fluorescence protein (GFP), β-lactamase and chloramphenicol acetyl transferase (CAT) genes. Besides these genes, the vector may contain another marker gene outside of the T-DNA sequence, preferably downstream of the left border sequences. The marker gene placed in that position is useful for evaluating the effectiveness of the modified border sequences.

The term "replication origin" as used in this specification means a specific DNA region in which the replication reaction is initiated, commonly called Ori.

(2) Transformation

To use the vector of the invention, a foreign gene for the intended transformation is inserted into the T-DNA region. The foreign gene to be inserted usually contains a promoter that can operate in the host plant and the structural gene encoding the characteristic to be conferred to the plant linked downstream of the promoter. If necessary, more than one gene may be linked together and, in addition or alternatively, a sequence for enhancing the efficiency of expression may be interposed between the promoter and the downstream structural gene before insertion into the T-DNA region.

Before being introduced into a target plant, the vector of the invention which harbors the foreign gene is introduced into a bacterial of *Agrobacterium* species capable of infecting the plant (e.g. *Agrobacterium tumefaciens*). To this end, various methods well known to the skilled artisan can be employed. For example, the vector may be transferred into the *Agrobacterium* by conjugation; if possible, the *Agrobacterium* may be directly transformed with the vector of the invention containing the foreign gene.

Conventional techniques may be employed to infect the plant with the *Agrobacterium* containing the vector of the invention and they include, for example, wounding part of the plant body and infecting it with the bacterium, infecting the callus with the bacterium, co-cultivating the protoplast and the bacterium, and co-cultivating slices of the leaf tissue together with the bacterium. The transformed cells obtained by these methods can be selected by using the suitable selection marker/s or assaying if they express the intended characteristic. The transformed cells may further be differentiated by the prior art technology to yield a recombinant plant body.

In order to integrate that T-DNA containing the foreign gene into the chromosomal DNA in the plant, the vir region is necessary. The vir region may be supplied from the vector having the foreign gene or from a different vector.

The plant cells transformed with the vector of the invention may be differentiated by the prior art technology to yield a recombinant plant body. The transformed plant may be selected by using a suitable selection marker or assaying if it expresses the intended characteristic.

Whether a DNA sequence/s unnecessary for the intended transformation has been integrated into plant chromosomes or not can be determined by various methods well known to the skilled artisan. For example, oligonucleotide primers are synthesized on the basis of the vector DNA sequence/s outside the borders and with these primers, PCR is performed to analyze the chromosomal DNA sequences in the transformed plant. In the case of transformation with a vector that contains a marker gene outside the T-DNA sequence, analysis can be done by assaying if the marker gene has been expressed.

The vector of the invention is characterized by its function to reduce the possibility of the integration of a DNA sequence/s unnecessary for the intended transformation. The term "to reduce the possibility of the integration" means that, compared to the use of a vector which is not modified on the left border sequence, the frequency of the integration of the unnecessary DNA sequence/s into host chromosomes is low, or the length of the integrated unnecessary sequence is short, or there is no such integration and; in addition or alternatively, compared to the use of a vector which is not modified on the left border sequence, the frequency of unintended transformation is low, or unintended transformation is slight, or there is no occurrence of such transformation. The term "DNA sequence unnecessary for the intended transformation" means a portion or fragment of the DNA sequence located outside the T-DNA sequence in the vector (namely, non-T-DNA). It does not matter whether it is functional by itself or encodes a polypeptide or protein.

Various plants can be transformed by the transforming method of the invention and they include monocotyledonous plants such as maize, sorghum, triticale, barley, oats, rye, wheat, onion and rice, and dicotyledonous plants such as soybean, alfalfa, tobacco, rape, sunflower, potato, pepper and tomato. The method of the invention can reduce the possibility of the integration of a DNA sequence/s unnecessary for the intended transformation into plant chromosomes and the transgenic plants obtained by using the transformation method are less likely to have unexpected characteristics. Therefore, the method of the invention is suitable for transforming plants that can be taken as food by other organisms and regarding which there is particular concern about the possibility that the non-T-DNA sequence/s will transfer into plant chromosomes by *Agrobacterium*-mediated transformation. The method is most suitable for transforming monocotyledonous plants, in particular, rice.

Unless otherwise noted, the term "plant or plants" as used in the specification covers not only a plant body (individual) but also its seed (germinated or immature), part (leaf, root, stem, flower, stamen, pistil or slices of these), culture cell, callus and protoplast.

EXAMPLE

Example 1

(1) Preparing Vectors

Plasmid vector pSB11 (Genbank Accession No. AB027256, Komari et al., Plant Journal 10, 165–174 (1966)) was modified to have within the T-DNA region a cassette for expressing the hygromycin resistance gene (HPT) by means of a ubiquitin promoter and a ubiquitin intron (Christensen et al., Plant Molecular Biology 18, 675–689 (1992) and into the plasmid, a cassette for expressing a catalase intron containing GUS gene (Ohta et al., Plant Cell Physiology 31, 805–813 (1990)) by means of a ubiquitin promoter was inserted at the site recognizable by restriction enzyme StuI. The thus prepared plasmid was designated pSLB0 (see FIG. 1 and SEQ ID:NO. 1). The nucleotide sequence of pSLB0 is shown as SEQ ID:NO. 1.

Figure 2:
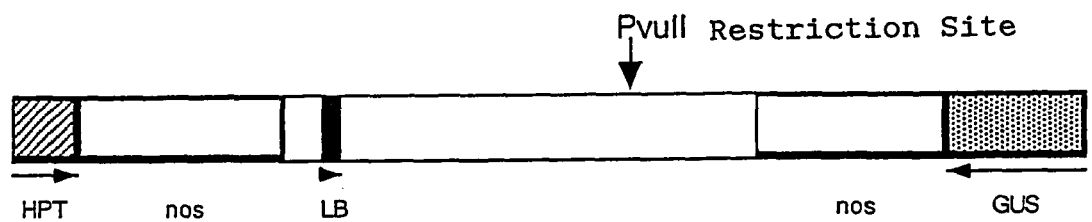
FIG. 2 shows maps of the areas of vectors pSLB0, pSLB2 and pSLB3 in the neighborhood of the left border sequence (which is hereunder sometimes referred to as LB). To prepare pSLB2 and pSLB3, a synthetic DNA fragment having two or three left border sequences was inserted into pSLB0 between LB and the GUS expressing cassette at the restriction site of PvuII. In pSLB2, two left border sequences were inserted by the synthetic DNA fragment (the inserted left border sequence/s is hereunder referred to as sLB) to give a total of three LBs, and in pSLB3, three sLBs were inserted by the synthetic DNA fragment to give a total of four LBs.
Figure 2:
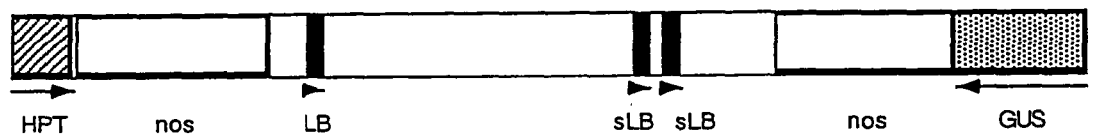
Figure 2:
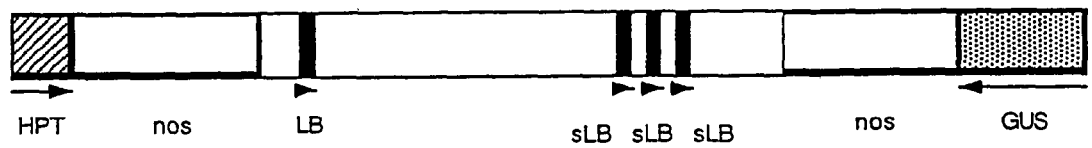

Then, based on the nucleotide sequence of Ti plasmid pTiAch5 (Genbank Accession No. K00548), a synthetic DNA containing a left border sequence (hereunder abbreviated as LB) and the complementary synthetic DNA were prepared, they were annealed and processed to form blunt ends, and then used to prepare DNA fragments respectively having two and three LB sequences. The nucleotide sequences of the two synthetic DNAs are shown as SEQ ID:NO. 2 and SEQ ID:NO. 3. Each of the DNA fragments was inserted into pSLB0 between LB and the GUS expressing cassette at the site recognized by restriction enzyme PvuII; in this way, vectors were prepared that had more than one LB attached. The vector having two of the LB introduced by the synthetic DNA (which is hereunder sometimes referred to as sLB) to give a total of three LBs was designated pSLB2, and the vector having three sLBs introduced to give a total of four LBs was designated pSLB3 (for the maps of areas of pSLB0, pSLB2 and pSLB3 in the neighborhood of the synthetic LBs, see FIG. 2). Each of these three plasmids was introduced into *Agrobacterium tumefaciens* LBA4404 which already had plasmid vector pSB1 introduced (Genbank Accession No. AB027255, Komari et al., Plant Journal 10, 165–174 (1996)). They were subjected to the following tests.

(2) Transformation

Calli derived from the immature embryo of rice variety "Asanohikari" were transformed with LBA4404(pSLB0), LBA4404(pSLB2) and LBA4404(pSLB3) in accordance with the method of Hiei et al. (Hiei et al., Plant Journal 6, 271–282 (1994)).

(3) Analysis of the Expression of GUS Gene in Transformants

Some leaves of the hygromycin-resistant plants obtained in Example 2 were stained with X-Gluc to check for the expression of the GUS gene. Seventeen out of the 340 plant individuals transformed with LBA4404(pSLB0) expressed the GUS gene, indicating that *Agrobacterium* derived DNA outside the border sequences was introduced into 5% of the plant individuals transformed with the conventional vector having only one LB. On the other hand, the number of plant individuals transformed with LBA4404(pSLB2) and LBA4404(pSLB3) and which expressed the GUS gene decreased with the increasing number of synthetic LBs (Table 1). This indicates that the integration of synthetic LBs into the vector decreased the likelihood for DNA beyond the left border sequence to be transferred to the plant.

(4) Analysis of Genomic DNA in the Individuals not Expressing the GUS Gene

In some of the individuals that did not express the GUS gene in (3), DNA beyond the left border sequence may have been introduced into plant chromosomes but not far enough to the ubiquitin promoter for triggering the expression of the GUS gene. To verify this possibility in each group of plants that did not express the GUS gene, about 60 independent transformants were randomly chosen and genomic DNA was extracted and subjected to PCR analysis. The primers used in PCR analysis were so prepared as to permit amplification of the region extending from a location between the inherent LB and the synthetic LB to a location in the GUS gene. The sequences of the primers are shown as SEQ ID:NO. 4 and SEQ ID:NO. 5.

As a result of the PCR analysis, seven out of the 67 plant individuals (10.4%) transformed with LBA4404(pSLB0) showed DNA amplification, revealing that when the conventional vector having only one LB was used, *Agrobacterium* derived DNA other than the desired T-DNA was integrated into chromosomes in the created transformants with a frequency of 10.4% of higher. In contrast, DNA amplification was found to take place in none of the plant individuals transformed with LBA4404(pSLB2) and LBA4404(pSLB3) that had synthetic LBs.

The results are shown in Tables 1 and 2.

TABLE 1

Analysis for the Expression of GUS Gene

| Vector | Number of transformants | Percentage of GUS expressing plants |
|---|---|---|
| pSLB0 | 340 | 5.0 |
| pSLB2 | 327 | 1.2 |
| pSLB3 | 370 | 0.8 |

TABLE 2

Analysis of Genomic DNA

| Vector | No. of plants from which DNA was extracted | No. of plants in which DNA was amplified by PCR |
|---|---|---|
| pSLB0 | 67 | 7 |
| pSLB2 | 55 | 0 |
| pSLB3 | 58 | 0 |

As can be seen from the above, the present invention decreased the integration of a DNA sequence/s outside the border sequences in plant chromosomes and made it possible to increase the efficiency of introducing only the intended T-DNA.

The foregoing description of the invention concerns primarily the use of two or more left border sequences, which may be derived from the same or different species of *Agrobacterium*. It should, however, be stressed that the fundamental concept of the invention lies in modifying the left border sequence in plant transformation vectors such that it can be recognized by vir proteins more efficiently to reduce the integration of any unnecessary non-T-DNA sequence to plant chromosomes. Therefore, the present invention embraces all vectors that have the modified left border sequence/s capable of achieving the same result. In addition to the examples described above, the modified left border sequences include the following: (1) those sequences which are derived from the sequence already existing in relevant plasmids by deletion, substitution or addition of one or more nucleotides in the existing left border sequence to be recognized by vir proteins more efficiently; (2) those sequences which are derived from the sequence already existing in the plasmid by deletion, substitution or addition of one or more bases in any sequence near the existing left border sequence to be recognized by vir proteins more efficiently; (3) those sequences which contain a plurality of any sequences that can be recognized by vir proteins; and (4) any combinations of (1)–(3).

What is claimed is:

1. A vector for *Agrobacterium*-mediated plant transformation comprising:
   a T-DNA right border region that is recognized by the vir proteins of *Agrobacterium*;

SEQUENCE LISTING

```
<160> NUMBER OF SEQ ID NOS: 1

<210> SEQ ID NO 1
<211> LENGTH: 11
<212> TYPE: PRT
<213> ORGANISM: Artificial Sequence
<220> FEATURE:
<223> OTHER INFORMATION: Description of Artificial Sequence: PEP1
      synthetic peptide

<400> SEQUENCE: 1

Asp Pro His Ile Lys Leu Gln Leu Gln Ala Glu
  1               5                  10
``` a T-DNA left border region comprising at least two T-DNA left border sequences that is recognized by the vir proteins of *Agrobacterium*;
   a T-DNA region located between these border regions and into which a nucleotide sequence to be introduced into the plant can be inserted; and
   a replication origin that enables replication of said vector in bacteria;
   wherein said vector when used in the *Agrobacterium*-mediated plant transformation reduces the integration frequency of a non-T-DNA segment into a plant chromosome, as compared with a vector comprising a T-DNA left border region consisting of a single T-DNA left border sequence.

2. The vector according to claim 1, wherein the T-DNA region contains a marker comprising a polynucleotide sequence that permits the selection of a plant transformed with the vector.

3. The vector according to claim 1, wherein the replication origin permits replication of the vector in a bacterial cell for vector amplification and an *Agrobacterium* host cell.

4. A method for transforming a plant cell comprising the steps of:
   introducing the vector according to any one of claims 1, 2 or 3 into an *Agrobacterium* host cell; and
   transforming a plant cell with the *Agrobacterium* host cell harboring the vector,
   thus obtaining a transformed plant cell.

5. A plant transformed by the method of claim 4.

6. A method for reducing the integration frequency of non-T-DNA segment of a vector for *Agrobacterium*-mediated plant transformation, comprising the steps of:

introducing the vector according to any one of claims 1, 2 or 3 into an *Agrobacterium* host cell; and transforming a plant cell with the *Agrobacterium* host cell harboring the vector, thus obtaining a transformed plant cell, wherein the integration frequency of non-T-DNA segment into the chromosome of the plant cell is reduced as compared to the case when a vector comprising a T-DNA left border region consisting of a single T-DNA left border sequence is used.

7. The vector according to claim 1, wherein the T-DNA left border region comprises at least three T-DNA left border sequences.

8. A method for transforming a plant comprising the steps of:

introducing the vector according to any one of claims 1, 2 or 3 into an *Agrobacterium* host cell; and transforming a plant by infecting the plant with the *Agrobacterium* host cell harboring the vector;

thus obtaining a transformed plant.

* * * * *

UNITED STATES PATENT AND TRADEMARK OFFICE
CERTIFICATE OF CORRECTION

| | |
|---|---|
| PATENT NO. | : 7,087,812 B1 |
| APPLICATION NO. | : 09/856976 |
| DATED | : August 8, 2006 |
| INVENTOR(S) | : Yoshiki Kuraya et al. |

It is certified that error appears in the above-identified patent and that said Letters Patent is hereby corrected as shown below:

Title Page,
Title of the invention Item (54), and Col. 1, Ln 1

"VECTORS FOR TRANSFORMING PLANTS" Should read -- PLANT TRANSFORMATION VECTORS; --.

Signed and Sealed this

Thirtieth Day of January, 2007

JON W. DUDAS
*Director of the United States Patent and Trademark Office*